US00PP28692P3

(12) United States Plant Patent
Larse

(10) Patent No.: US PP28,692 P3
(45) Date of Patent: Nov. 28, 2017

(54) STRAWBERRY PLANT NAMED 'PLAYA'

(50) Latin Name: *Fragaria×ananassa*
Varietal Denomination: Playa

(71) Applicant: John Larse, Aptos, CA (US)

(72) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 14/545,385

(22) Filed: Apr. 29, 2015

(65) Prior Publication Data

US 2016/0324050 P1 Nov. 3, 2016

(51) Int. Cl.
*A01H 5/08* (2006.01)

(52) U.S. Cl.
USPC ..... Plt./209

(58) Field of Classification Search
USPC ..... Plt./208, 209
See application file for complete search history.

(56) References Cited

PUBLICATIONS

Trademark citation on "NAIA", published Feb. 28, 2012.*

* cited by examiner

*Primary Examiner* — Anne Grunberg
(74) *Attorney, Agent, or Firm* — Cooley LLP

(57) ABSTRACT

The present invention provides a new and distinct strawberry plant designated as 'Playa' (a.k.a. '108926').

5 Drawing Sheets

Latin name of the genus and species: *Fragaria×ananassa.*
Varietal denominations: 'Playa' (a.k.a. '108926').

BACKGROUND OF THE INVENTION

The present invention relates to a new and distinct strawberry variety designated as 'Playa' (a.k.a. '108926').

'Playa' (a.k.a. '108926') is the result of a controlled-cross between a female parent cultivar designated 107707 and a male parent cultivar designated 103474 (both unpatented, proprietary cultivars) made by the Inventor and was first fruited in Watsonville, Calif. growing fields. Following selection and during testing, the plant was originally designated '108926' and subsequently named 'Playa'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduces true to type in successive generations of asexual reproduction.

BRIEF SUMMARY OF THE INVENTION

This invention relates to new and distinctive strawberry cultivar designated as 'Playa'. These cultivars are primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish strawberry variety 'Playa' from known strawberry varieties. In addition, this new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The fruit produced by this new cultivar is attractive and of excellent quality.

DESCRIPTION OF THE DRAWINGS

The accompanying color photographs depict various characteristics of the cultivars as nearly true as possible to make color reproductions.

DETAILED DESCRIPTION OF THE INVENTION

'Playa' (a.k.a. '108926')

Figure 1:
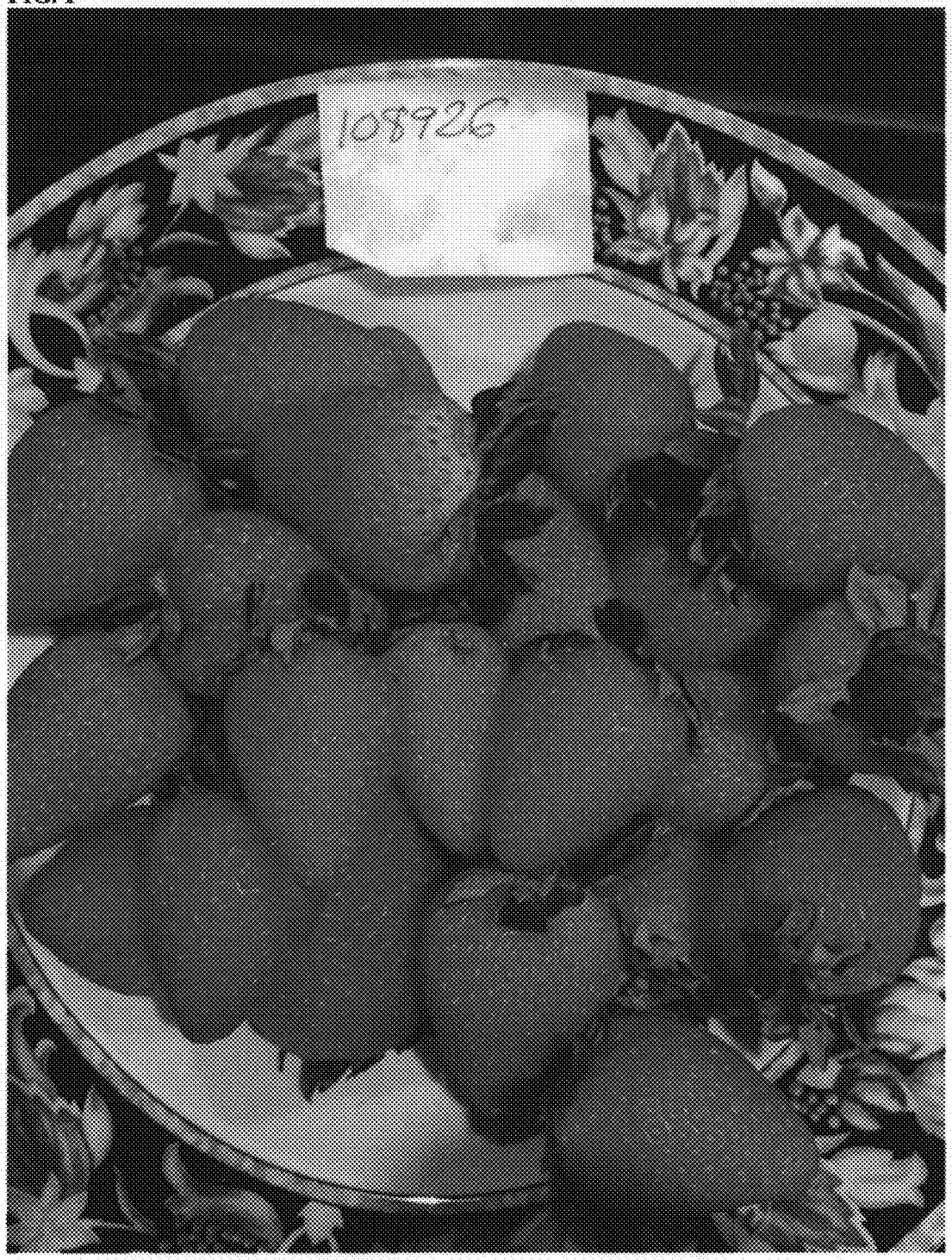
FIG. 1 shows ripe fruits of 'Playa'.
Figure 2:
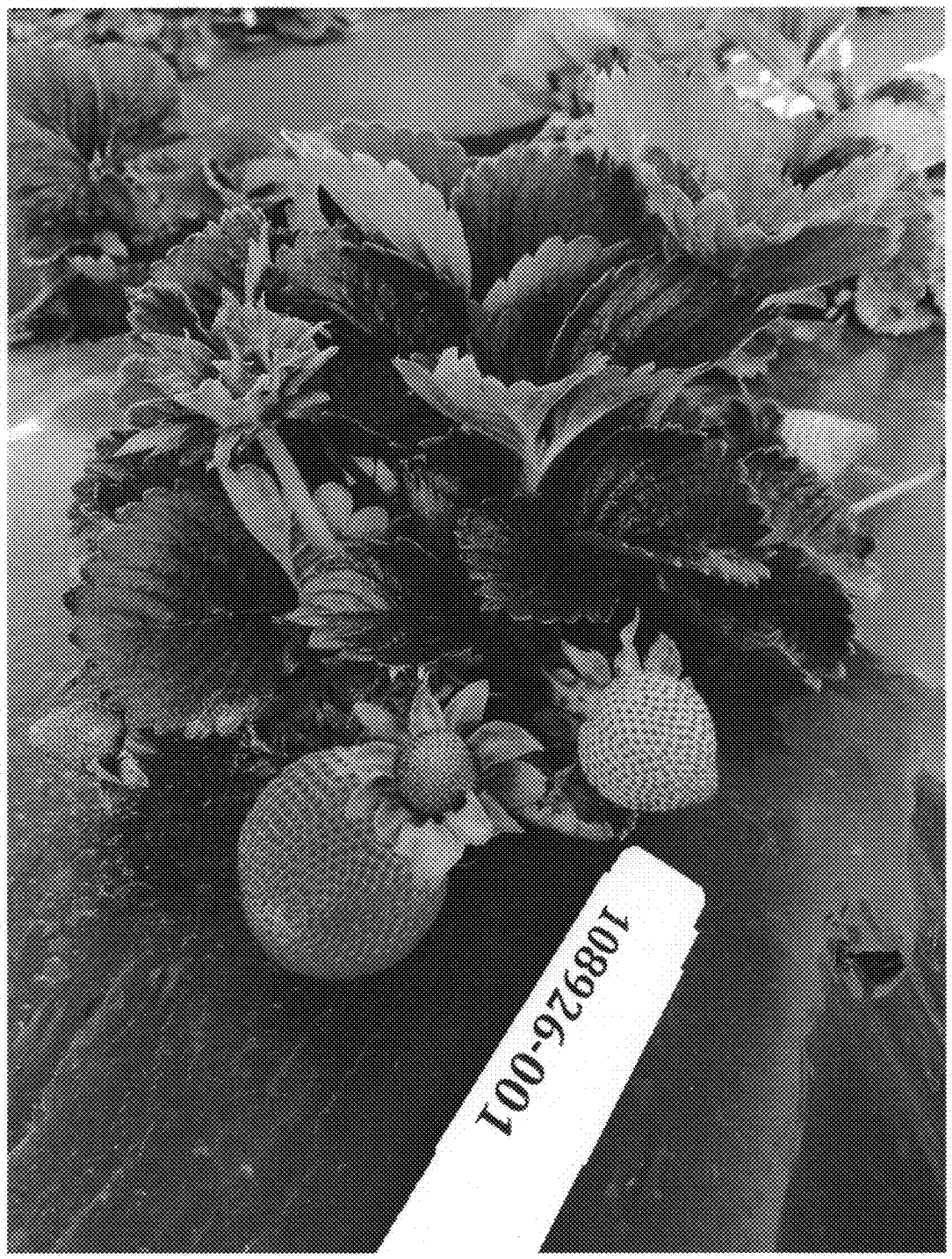
FIG. 2 shows 'Playa' plants in the field with ripe and near-ripe fruits.
Figure 3:
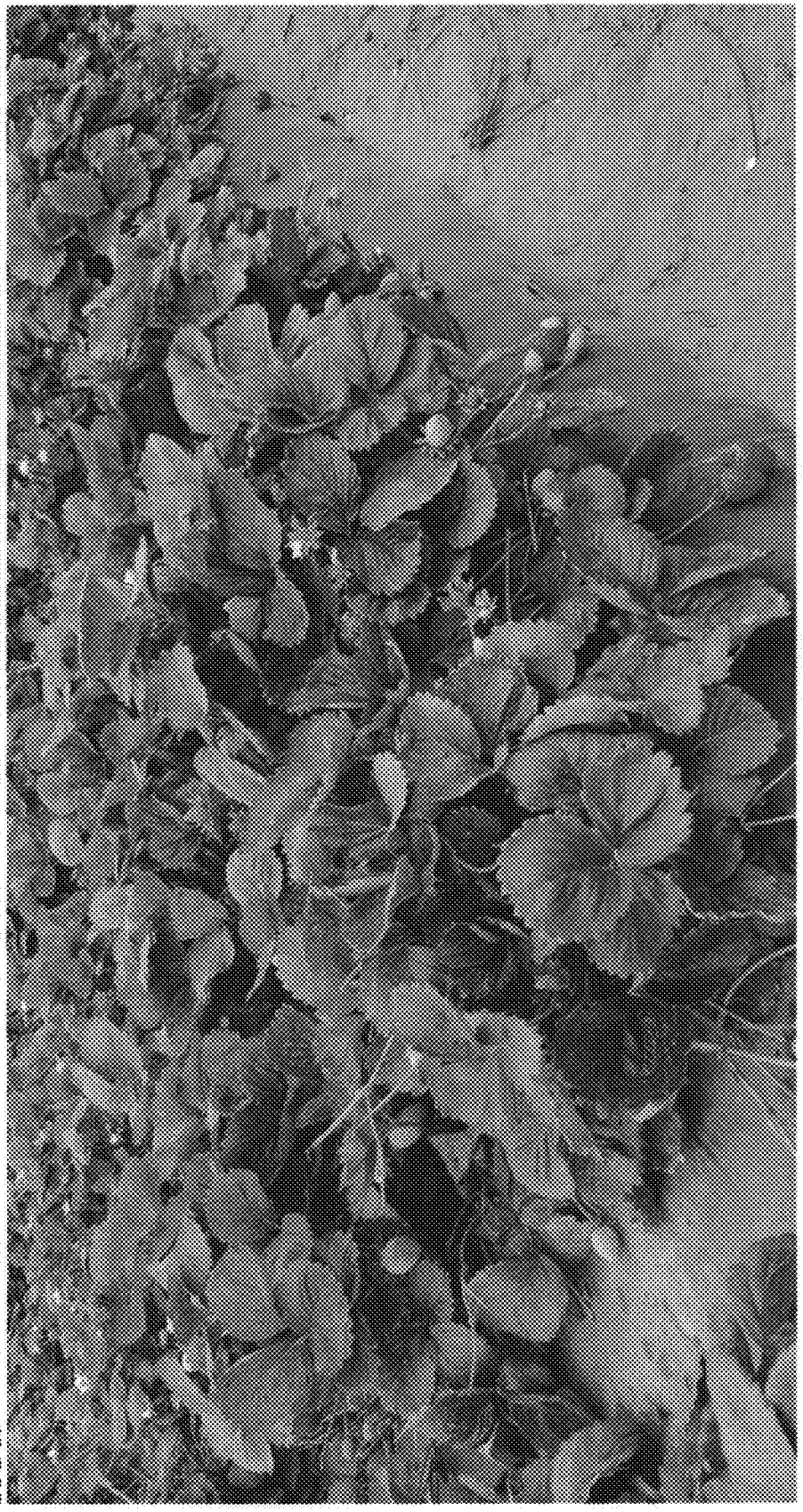
FIG. 3 shows 'Playa' plants growing in the field.
Figure 4:
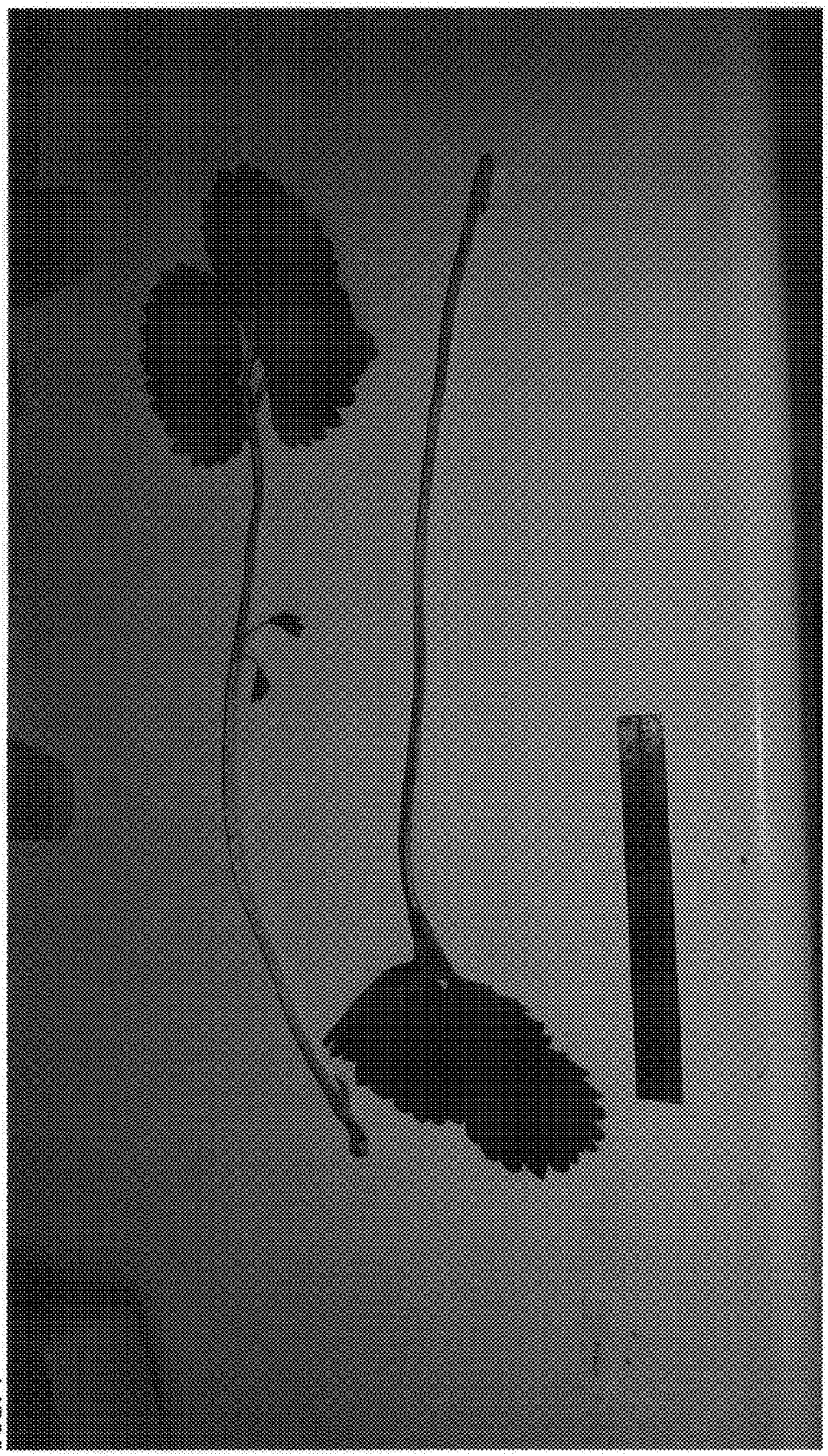
FIG. 4 shows 'Playa' plant leaves with petioles.
Figure 5:
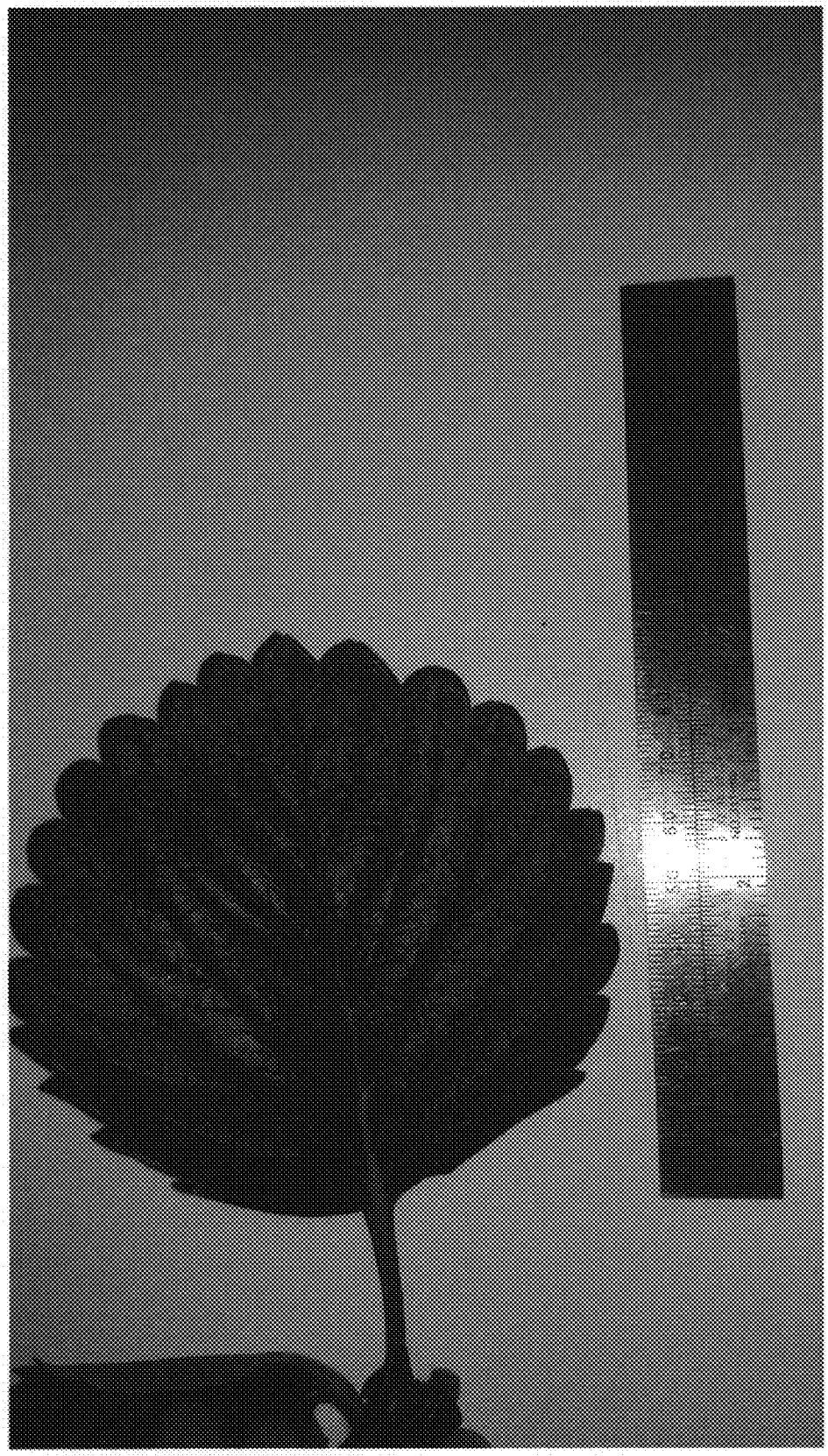
FIG. 5 shows a close-up look of a 'Playa' plant leaf.

This invention relates to a new and distinctive strawberry cultivar designated as 'Playa'. It is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits in combination distinguish strawberry variety 'Playa' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

'Playa' has not been observed under all possible environmental conditions, and the phenotype may vary significantly with variations in environment. The following observations, measurements, and comparisons describe this plant as grown under normal conditions in Watsonville, Calif. unless otherwise noted.

Hybrid Patent Data Sheet
(planted: October Year 1; measurement: November Year 2)
Variety: PLAYA (A.K.A. '108926')

| Plant | |
|---|---|
| Plant Growth Habit | Semi-upright |
| Day length | neutral |
| Planting Season | fall |
| Height (mm) | 380 |
| Diameter (mm) | 360 (the entire plant structure, including the "superstructure" of petioles, leaves, flowers)<br>70 (inner "base" or "heart" structure of the plant, i.e. the mature apical and axial crowns of the strawberry plant where petioles, flowers and runners are attached) |
| Density of foliage | heavy |
| Average number of crowns per mature plant | 4 |
| Plant vigor | high |
| Rain/weather tolerance (e.g., high, moderate, or low) | moderate |
| Harvest Ease | moderate |
| **Terminal Leaf** | |
| Length (mm) | 99 |
| Width (mm) | 91 |
| Terminal leaflet length/width ratio | 0.9 |
| Blistering | none |
| Terminal leaf shape | orbicular |
| Number of teeth/terminal leaflet: | 20 |
| Shape of the terminal leaflet base | obtuse |
| Shape of terminal leaflet in cross-section | concave |
| Margin description of the terminal | serrate |
| Shape of teeth | obtuse |
| Color of upper side of leaves | 137A |
| Color of lower side of leaves | 139C |
| Leaf glossiness | medium to weak |
| presence or absence of any leaf variegation | absence |
| Number of leaflets | 66 |
| Terminal Leaflet margin | flat |
| Terminal Leaflet shape of apex | rounded |
| **Petiole** | |
| Length (mm) | 244 |
| Width (mm) | 4 |
| Petiole pubescence | medium |
| Petiole pose of hairs | outwards |
| Petiole color | 145B |
| Attitude of hairs on petiole and pedicel | Outwards to horizontal |
| **Petiolule** | |
| Length (mm) | 48 |
| Width(mm) | 3.2 |
| **Stolon** | |
| Diameter (mm) | 4 |
| Stolon color | 145A |

-continued

Hybrid Patent Data Sheet
(planted: October Year 1; measurement: November Year 2)
Variety: PLAYA (A.K.A. '108926')

| | |
|---|---|
| Widest diameter of stolon at point of attachment of leaf (mm) | 4.78 |
| Stolon anthocyanin | 187A |
| Density of pubescence on the stolon | Medium |
| Stolon number | 2 to 12 |
| Stolon thickness | Large |
| Stolon attitude | outwards |
| Stolon size | medium to large |
| **Inflorescence** | |
| Petal/flower | NA |
| Inflorescence position relative | even |
| Number of flowers per plant | 30-40 |
| Fertility | self-fertile |
| Time of flowering | March to April |
| Corolla (mm) | 13 |
| Calyx (mm) | 5 |
| Calyx color | 137C |
| Position of calyx attachment | inserted |
| Level of adherence of calyx | High |
| Petal length (mm) | 17 |
| Petal width (mm) | 7 |
| Petal per flower | 5 |
| Flower arrangement of petals | free to touching |
| Upper petal color | 155C |
| Lower petal color | 155D |
| Sepal length (mm) | 19 |
| Sepal width (mm) | 9 |
| Sepals per flower | 10 |
| Peduncle size (cm) | 22.5 |
| Stipule height (mm) | 27 |
| Stipule width (mm) | 11 |
| Stipule attitude | upwards |
| Stipule coloration | 145B |
| Pedicel coloration | 145A |
| Anther coloration | 12A |
| Stamen count | 22 |
| Stamen shape | dorsifixed |
| Stamen length (mm) | 4.03 |
| **Fruit** | |
| Fruit/truss | 1-5 |
| Length (mm) | 37 |
| Width (mm) | 29 |
| Fruit length/width ratio | 1.27 |
| Core length (mm) | 30 |
| Core width (mm) | 9 |
| Glossiness | medium |
| Fruiting truss attitude | erect |
| Fruit skin color | 41A |
| Evenness of fruit color | medium |
| Predominant fruit shape | long-conical |
| Difference in shape between primary & secondary fruits | none to very slight |
| Width of the band without achenes | medium |
| Position of the achenes | inserted |
| Number of achenes per fruit | 257 |
| Achene weight (g) | 0.18 |
| Achene coloration | 152D |
| Flesh color | 45A |
| excluding core | 41A |
| Color of fruit core | 41A |
| Firmness of flesh | firm |
| Texture when tasted | medium |
| Time of fruit ripening | April |
| Harvest maturity (50% of plants with ripe fruit) | early |
| Grams of fruit/plant (g) (During peak season, June) | 678 |
| Appearance Score (from 1-5, with 5 = best) | 4 |
| Storage longevity (e.g., 10 days to 29 days-13 days weeks) | |

-continued

| Hybrid Patent Data Sheet (planted: October Year 1; measurement: November Year 2) Variety: PLAYA (A.K.A. '108926') | |
|---|---|
| Cull rate: Non salable fruit production rate | <10% |
| Disease and pest resistance | Not tested |
| Acidity as measured by pH | 3.26 |
| Sweetness as measured by brix | 9 |

When 'Playa' is compared to the proprietary female parent, 'Playa' has a lower height. The density of foliage of 'Playa' is heavy, while the density of foliage of the female parent is medium.

When 'Playa' is compared to the proprieiary male parent, 'Playa' has stolons that are much thicker than the stolons of the male parent. Additionally, 'Playa' presents smaller tri-foliate leaflets and much larger and fruit than the male parent.

When 'Playa' is compared to 'Seascape' (U.S. Plant Pat. No. 07,614), 'Playa' has a density of foliage that is heavy, while the density of foliage of Seascape' is light. The plant vigor of 'Playa' is high, while the plant vigor of 'Seascape' is moderate. The leaf glossiness of 'Playa' ranges from medium to weak, while the leaf glossiness of 'Seascape' is medium. The number of leaflets of 'Playa' is 66, while the number of leaflets of 'Seascape' is 49. 'Playa' presents larger fruit than 'Seascape' as well. 'Playa' tri-foliate leaves have a more serrate shape relative to the crenate leaves of 'Seascape'.

The invention claimed is:

1. A new and distinct cultivar of strawberry plant named 'Playa' substantially as shown and described herein.

* * * * *